United States Patent [19]
Zeff et al.

[11] 4,230,096
[45] Oct. 28, 1980

[54] METHOD OF IMPLANTING TRANSCUTANEOUS CONNECTOR

[76] Inventors: Robert H. Zeff, 4220 Foster Dr.; Steven J. Phillips, 6023 N. Waterbury Rd., both of Des Moines, Iowa 50312

[21] Appl. No.: 939,884

[22] Filed: Sep. 5, 1978

Related U.S. Application Data
[62] Division of Ser. No. 817,728, Jul. 21, 1977.

[51] Int. Cl.³ ............................................ A61B 17/00
[52] U.S. Cl. ......................................... 128/1 R; 3/1; 128/334 R
[58] Field of Search ............... 128/1 R, 303 R, 334 R, 128/348, 92 A; 3/1, 1.9

[56] References Cited

U.S. PATENT DOCUMENTS

| | | | |
|---|---|---|---|
| 2,439,995 | 4/1948 | Thrailkill | 128/92 A |
| 2,760,488 | 8/1956 | Pierce | 128/92 A |
| 3,540,451 | 11/1970 | Zeman | 128/334 R |
| 3,687,129 | 8/1972 | Nuwayser | 128/334 R |
| 3,809,075 | 5/1974 | Matles | 128/92 A |
| 3,878,565 | 4/1975 | Sauvage | 128/334 R |
| 3,947,897 | 4/1976 | Owens | 3/1.9 |

Primary Examiner—Dalton L. Truluck
Attorney, Agent, or Firm—Zarley, McKee, Thomte, Voorhees & Sease

[57] ABSTRACT

A transcutaneous connector is routed from within the internal regions of the body through an aperture formed in a bone located closely adjacent the outer body skin such as the iliac crest. An air tube connector extends from a balloon heart pump within the body through the iliac crest and is connected to an external gas drive means.

7 Claims, 6 Drawing Figures

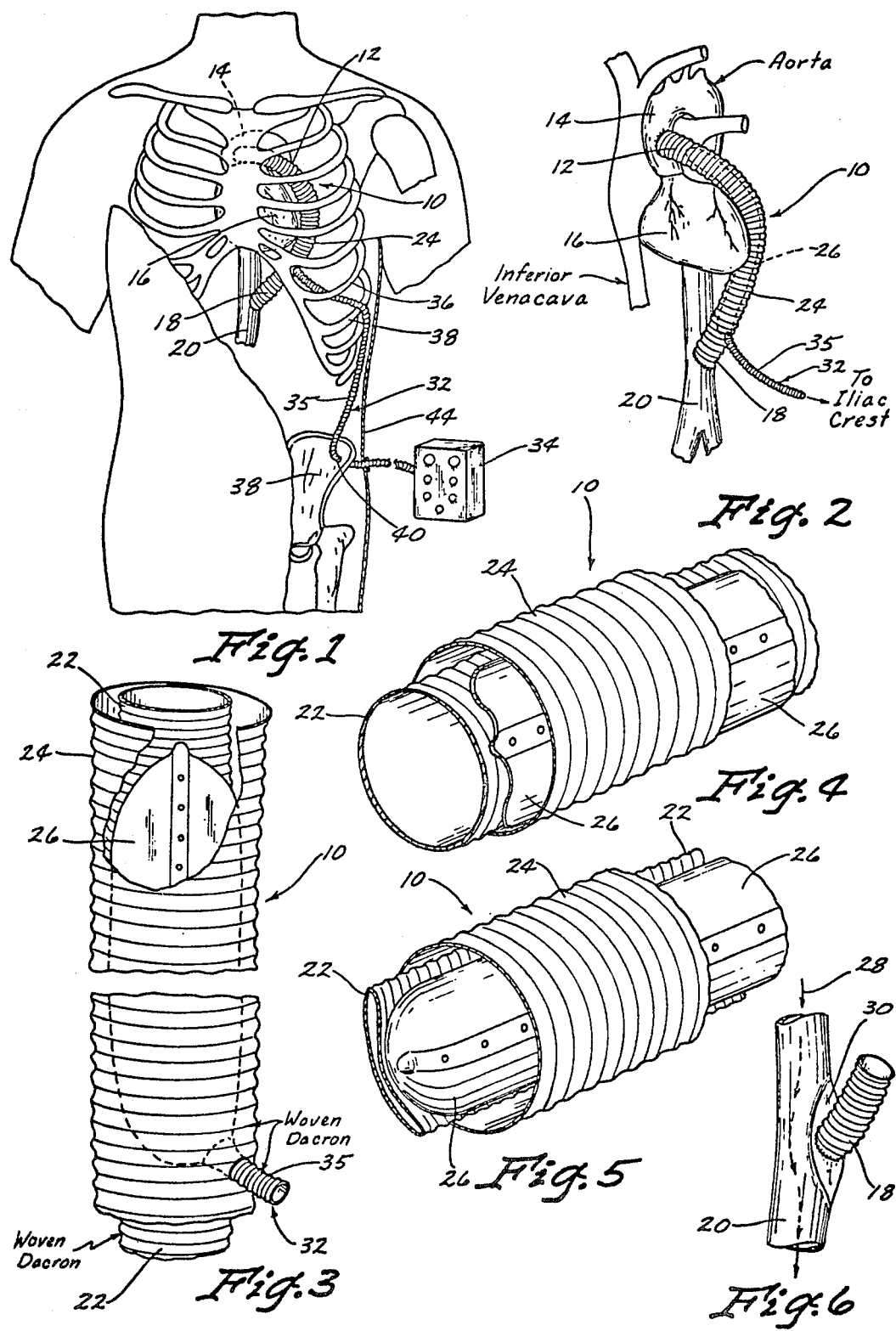

METHOD OF IMPLANTING TRANSCUTANEOUS CONNECTOR

This is a division of application Ser. No. 817,728, filed July 21, 1977.

BACKGROUND OF THE INVENTION

Assisted circulation techniques are an outgrowth of extracorporeal pump oxygenated systems developed in the mid-1950's. These techniques have been applied to patients for temporary assisted circulation, and more recently, for permanent left ventricular assistance. Most of the experimental and clinical application of these assist devices are based on the principle of diastolic augmentation. This is a system of counterpulsation where an external energy source delivers a pulsatile wave into the central circulation during cardiac diastole, and relaxes during cardiac systole. This is done by timing with the patient's electrocardiogram or pressure wave form.

This allows the following:
1. The stroke volume per unit work of the left ventricle is increased.
2. The diastolic perfusion pressure and ratio of mean diastolic pressure to mean systolic pressure is increased.
3. Coronary flow increases preferentially with diastolic pressure since coronary vascular resistance is minimal during cardiac diastole.
4. Coronary collateral flow to ischemic region of the myocardium is increased.
5. The modification of pulse pressure distribution in the aorta favors the increase of flow to vital organs.

This principle has been applied since the mid-1960's as a temporary form of cardiac assistance for patients in acute heart failure with a commercially available intra-aortic balloon pump.

A permanent booster heart, based on the principles described above should have the following features:
1. Effective hemodynamic support for the failing left ventricle.
2. Be designed so that intermittent as well as continuous use can be achieved.
3. Be failure free over long periods.
4. Have a size and shape that interfer minimally with other organs.
5. Be constructed of biologically compatible materials.
6. Be implanted with a tolerable surgical risk.
7. Be controlled reliably under varying physiologic conditions.
8. Have a portable power source to allow the patient free movement.
9. The transcutaneous connector should be constructed in such a way to facilitate easy connection to the power source with minimal risk of infection.

Some attempts at implantation of a permanent left ventricular assist device over the past 10-12 years have met with limited success. The pioneer in this field is, Dr. Adrian Kantrowitz, who implanted (in 1965 and 1966) a mechanical U-shaped auxiliary ventricle in two patients. Problems occurred with synchronization and clotting in these patients. In 1970 through 1972, again under Dr. Adrian Kantrowitz, Dr. Steven Phillips did some definitive experimental work with the hemodynamic effects of a dynamic aortic patch in animals and, with Kantrowitz, implanted two such devices in patients. One patient did not survive the surgery. The second survived but died of infection a few months later that occurred via the transcutaneous connector. A third attempt in 1976 by Dr. Kantrowitz to implant another device was only successful short-term as the patient also died of ascending infection from the transcutaneous connector.

These above devices of Kantrowitz were implanted with utilization of the heart-lung machine and were based on the principle of diastolic augmentation. A transcutaneous connector required a skin button that ultimately caused the patients demise due to ascending infection.

SUMMARY OF THE INVENTION

In 1977 at Mercy Hospital, Des Moines, Iowa, Dr. Steven J. Phillips and Dr. Robert H. Zeff implanted a permanent left ventricular assist device in a patient. This device was implanted without the use of extra-corporeal circulation and utilized existing materials that are commercially available for human implantation. The device itself consists of a woven Dacron graft on the outside of which is mounted a pumping chamber. This entire system again is covered with a woven Dacron graft. The proximal end of the graft is sewn to an incision made in the ascending aorta and the distal end of the graft is sewn to an incision made in the distal descending thoracic aorta. The transcutaneous connecting tube is wrapped in Dacron Velour material and is tunneled through the chest wall through the subcutaneous tissues of the trunk, is brought out through a hole drilled in the iliac crest to the skin where it is connected to the extra-corporeal power driving source.

The stroke volume of this pulsatile aortic chamber is 30-45 cc. The diameter and pumping chamber sizes of this booster heart will vary with the size of the patient and the stroke volume desired.

Its advantages are as follows:
1. Implantation does not require use of extra-corporeal circulation.
2. Materials used have all been demonstrated to be biocompatible and certified for non-experimental or frequent clinical human use.
3. It is felt the major risk of any permanent left ventricular assist device is ascending infection through the transcutaneous connector.

By passing the transcutaneous connector through bone it is felt that the risk of infection is significantly reduced to the point that should allow long-term survival of the patient. This is because: (1) the bone fixes the tube in place, reducing its motion of tissue irritation; and (2) resists ascending infection by nature of its physiology. The transcutaneous connector in this case, as not in the cases of previously implanted permanent devices, is much smaller and of biocompatible material.

The physiology of the patient in chronic left ventricular failure is as follows. The normal stroke volume of the left ventricle is approximately 80 cc. Cardiac reserve is such that chronic left heart failure does not occur until that stroke volume falls to the range of 40-50 cc. It is felt that if 30-40 cc stroke volume can be added to the patient by an external power source then theoretic recovery function can occur. A permanent left ventricular assist device as described can do this. By adding a 30-40 cc stroke volume to a patient in chronic failure, the patient should be allowed to return to a more normal function. Continuous pumping is not necessary. Intermittent pumping for a few hours a day and eventually a few days a week should be enough to allow the patient to remain in a clinically healthy state. This concept is similar to the concept of renal dialysis where a patient who has no functioning kidneys can be periodically and intermittently hooked up to a kidney machine. Between these hookups the patients can return to a more normal life. This can be the case with an artificial booster heart. Portable pumping as well as hospital, home and intermittent treatments can be carried to allow the patient to remain in a physiologic healthy state.

DESCRIPTION OF THE DRAWINGS

FIG. 1 is a front elevational view of the permanent left ventricular device implanted in the body.

FIG. 2 is an enlarged fragmentary view of the heart and aorta connected to the ventricular assist device.

FIG. 3 is an enlarged view of the parallel inner and outer aorta tubes having an inflatable balloon therebetween.

FIG. 4 is a view similar to FIG. 3 showing the balloon in its deflated condition.

FIG. 5 is a view similar to FIG. 4 showing the balloon inflated with the intertube substantially collapsed.

FIG. 6 is an enlarged view of the air tube grafted to the aorta while blood continues to flow therethrough.

DESCRIPTION OF THE PREFERRED EMBODIMENT

The parallel aorta balloon pump is generally referred to in FIG. 1 by the reference numeral 10 and is shown in FIG. 2 connected at its upper end 12 to the ascending aorta 14 in close proximity to the heart 16 while the lower end 18 is connected to the descending thoracic aorta 20. The balloon pump 10, as seen in FIG. 3, includes an inner tube 22 and an outer tube 24 between which an inflatable balloon 26 is positioned. The opposite ends of the tubes 22 and 24 are grafted to the aorta, as seen in FIG. 6, wherein the end 18 is grafted to the descending thoracic aorta 20 while blood continues to flow through the aorta as indicated by the arrows 28. A small fold 30 is made in the aorta 20 and an opening is formed only sufficiently large to accommodate the grafting of the tube ends thereto. Flow of blood through the aorta 20 is not impaired during this grafting procedure and thus a lung and heart machine is not required for this operation.

The tubes 22 and 24 are formed from biocompatible material such as woven Dacron Valour material available from U.S. Catheter, Instruments of America, Ithaca, New York. An intra-aortic balloon pump may be purchased from Datascope Corporation, Paramus, New Jersey.

The balloon 26 is connected by an inner tube 32 to a control unit 34 outside the body. The tube 32 is also wrapped with woven Dacron 35 and thus provides a biocompatible material in contact with body tissue. As seen in FIG. 1, the tube 32 extends between the ribs 36 and 38 downwardly to the iliac crest 40 where the tube exits through a hole 42 at the iliac crest. This routing of the tube 32 assures that it is held firmly minimizing irritation and possible infection to the body. The tube exits from the body at a point where there is minimum flesh as there is substantially only skin 44 over the iliac crest at the point where the tube 32 exits from the body. The bone in the iliac crest cannot become infected and thus risk of infection around the tube is substantially eliminated.

In FIGS. 4 and 5 the balloon 26 is shown in the deflated and inflated conditions, respectively. The control unit 34 is in turn connected to an inner source which synchronizes the pulsations of the pump 10 with the operation of the heart 16 such that they are 180° out of phase with each other. The blood pumped by the pump 10 will substantially move upwardly in the inner tube 22 towards the heart during cardiac distole. The pump 10 will be at rest during cardiac systole.

The inner and outer tubes 22 and 24 are approximately 16 to 18 inches long with the balloon 26 being approximately 14 inches in length. The inner tube 22 is 22 mm. in diameter while the outer tube is approximately 25 mm. The balloon 26 has a diameter of approximately 12 mm. The flow capacity of the tube 22 should be approximately equal to the aorta. Air is introduced into the balloon 26 at the bottom end and thus inflates upwardly forcing blood upwardly towards the heart during each pulsation. The tubes 22 and 24 are substantially straight throughout their length in the sense that there are no sharp turns or volume variations thereby eliminating undesirable turbulence within the tube 22 or the aorta. The driving unit for supplying air to the heart pin, including the control unit 34, is available from Datascope Corporation, Paramus, New Jersey.

It is understood that the method of implanting a transcutaneous connector by routing the connector tube through the iliac crest bone for operating a heart pump is only exemplary of the general application this method has since any organ within the body cavity could be connected to the tube connector for transmission of fluids in or out of the body cavity. The outer end of the tube may or may not be connected to a pumping apparatus or the like. Obviously, the selection of the iliac crest as the bone through which the connector tube is routed represents the most reasonable bone for this purpose but other bones could be appropriately utilized and still enjoy the benefits of this implanting method.

I claim:

1. A method of implanting a transcutaneous tube connector, comprising the steps of
    forming a tube connector aperture in a bone located closely adjacent the body outer skin, and
    routing the tube connector from the body cavity where it is connected to a body organ through said aperture and outwardly through the skin for transmission of fluid between the body cavity and the outside.

2. The method of claim 1 wherein routing the connector comprises routing a connector of biocompatible material through said aperture and outwardly through the skin.

3. The method of claim 1 wherein routing the connector comprises routing a connector of woven Dacron Velour material through said aperture and outwardly through the skin.

4. The method of claim 1 wherein forming a connector aperture in a bone comprises forming a connector aperture through the iliac crest.

5. The method of claim 1 further comprising the step of maintaining said connector in said aperture to reduce the motion of said connector.

6. The method of claim 1 wherein the step of routing the connector comprises routing an air tube from a balloon heart pump in the body to outside the body for connection to a gas drive means.

7. A method of implanting a transcutaneous connector, comprising the steps of,
    forming a connector aperture through the iliac crest bone in the vicinity of the place of exit from the body, and routing the connector through said aperture and outwardly through the skin.

* * * * *